(12) United States Patent
George et al.

(10) Patent No.: US 7,172,602 B2
(45) Date of Patent: Feb. 6, 2007

(54) PENILE PROSTHESIS IMPLANT INSERTION TOOL

(75) Inventors: Stephanie A. George, St. Louis Park, MN (US); James A. Gohman, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 816 days.

(21) Appl. No.: 10/373,647

(22) Filed: Feb. 24, 2003

(65) Prior Publication Data

US 2004/0010244 A1 Jan. 15, 2004

Related U.S. Application Data

(60) Provisional application No. 60/358,791, filed on Feb. 22, 2002, provisional application No. 60/383,464, filed on May 24, 2002.

(51) Int. Cl.
*A61F 11/00* (2006.01)
*A61F 5/00* (2006.01)

(52) U.S. Cl. ........................ 606/108; 600/40
(58) Field of Classification Search ........ 606/106–108; 600/40
See application file for complete search history.

(56) References Cited

U.S. PATENT DOCUMENTS

| | | | |
|---|---|---|---|
| 4,244,370 A | 1/1981 | Furlow et al. | 128/303 |
| 4,628,912 A | 12/1986 | Fischell | |
| 5,484,450 A | 1/1996 | Mohamed | 606/108 |
| 7,066,878 B2 * | 6/2006 | Eid | 600/40 |

FOREIGN PATENT DOCUMENTS

WO WO 2004/045421 A1 * 6/2004

* cited by examiner

*Primary Examiner*—Vy Bui
(74) *Attorney, Agent, or Firm*—Jose W. Jimenez; Kimberly K. Baxter

(57) ABSTRACT

A device for inserting a penile implant prosthesis through an incision into a corpus cavernosum is provided. The device includes an elongated, rigid body having a tip portion and tail portion, the tip portion including two prongs extending in a tip direction and a center portion between the two prongs, the prongs and center portion defining a notch adapted to engage and exert a force along the tip direction on a corner where a cylinder portion and a pump tubing of the prosthesis join each other, the prongs and center portion further defining a recess on one side of the center portion, the recess adapted to at least partially receive the cylinder portion or the pump tubing. The elongated body of the device defines a channel disposed along a substantial portion of the elongated body. The tail portion of the elongated body can be formed as a paddle adapted to be inserted between the cylinder and tissues near or at the incision to prevent puncturing of the cylinder when the incision is being sutured closed. The tail portion can also be a rounded tail end adapted to engage an end of the cylinder portion for pushing the cylinder portion into the corporal body. The tip portion can extend either in a direction parallel to the longitudinal axis of the elongated body or form an angle with it, depending on the desired operation.

13 Claims, 7 Drawing Sheets

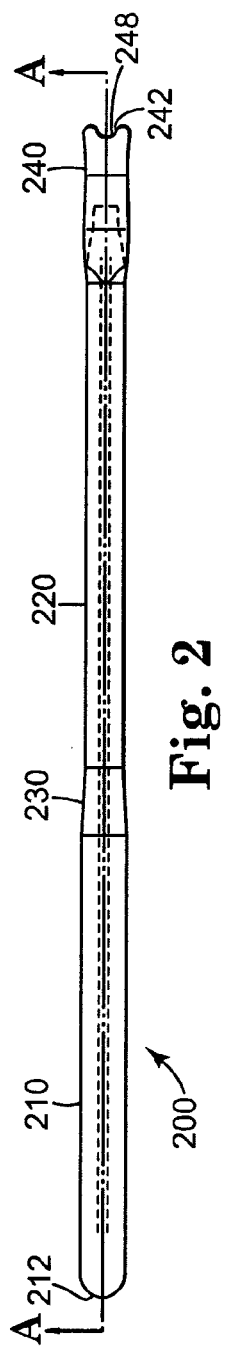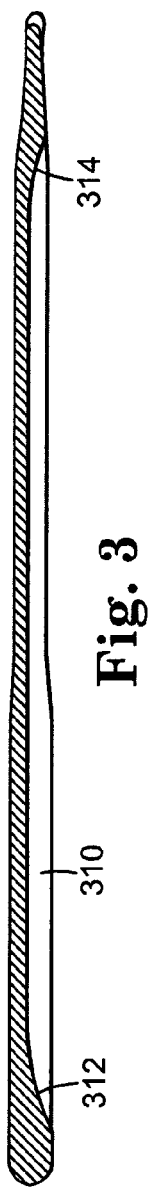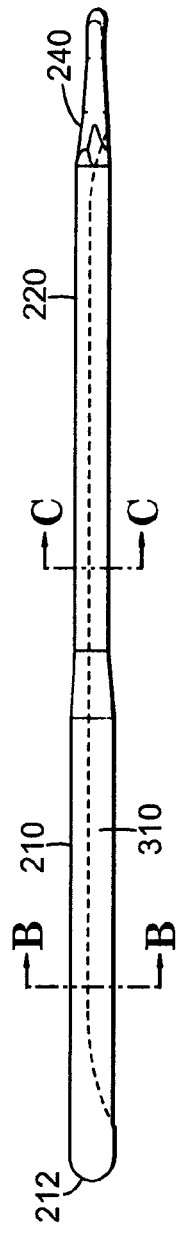

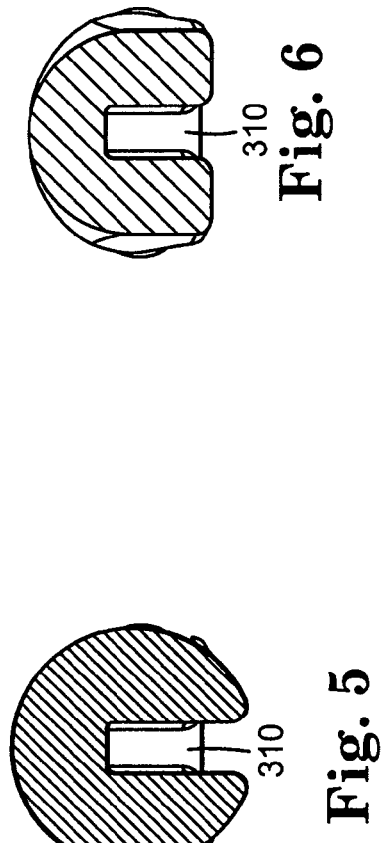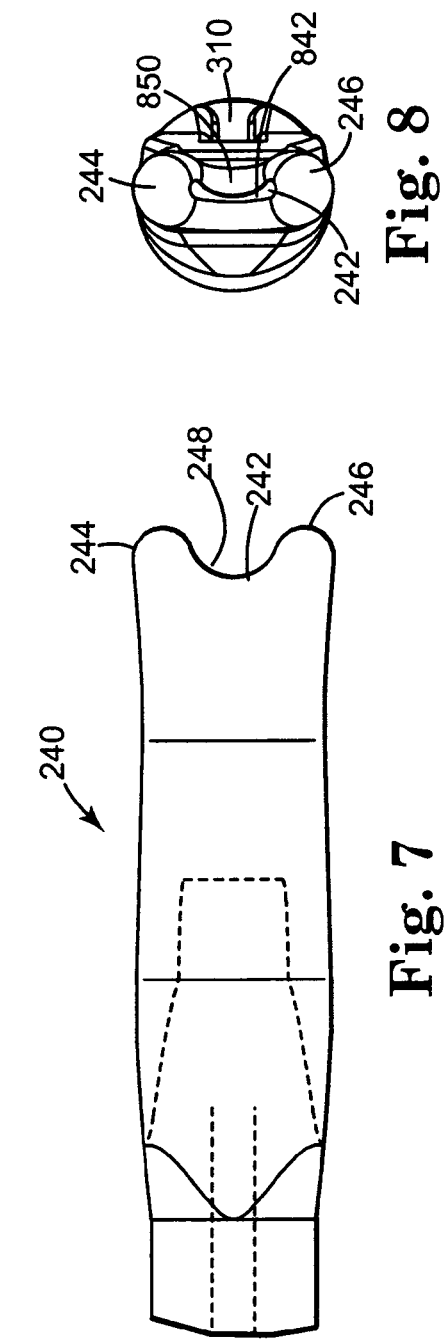

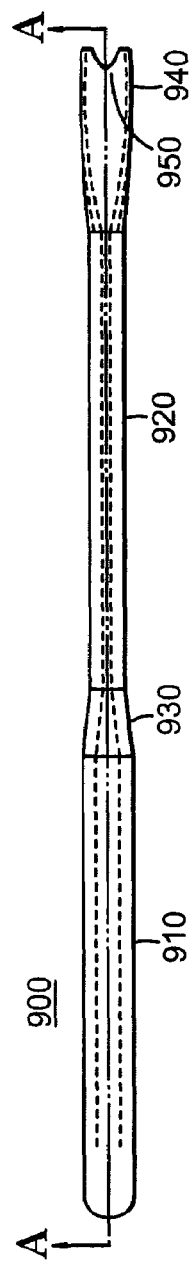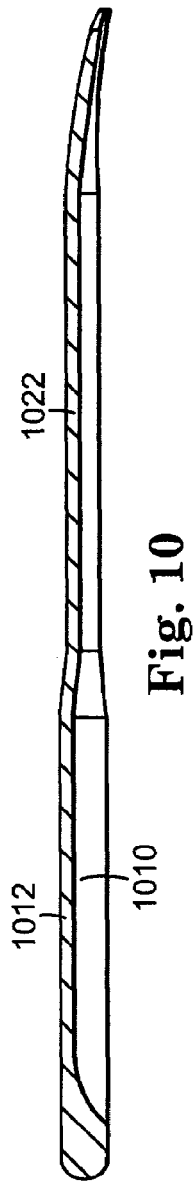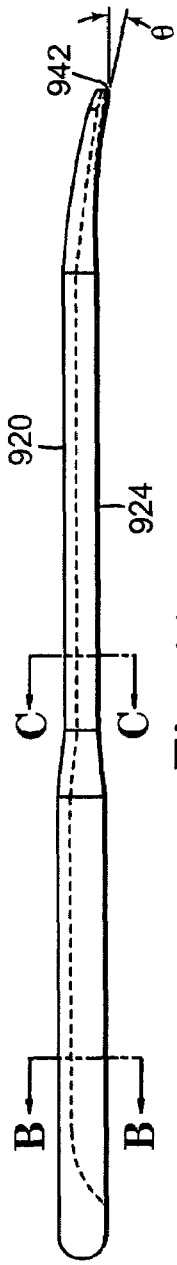

PENILE PROSTHESIS IMPLANT INSERTION TOOL

CROSS REFERENCE TO RELATED APPLICATION

The present application claims to the benefit of the U.S. Provisional Application No. 60/358,791, filed Feb. 22, 2002, and the U.S. Provisional Application No. 60/383,464, filed May 24, 2002, both of which are incorporated herein by reference.

FIELD OF THE INVENTION

The invention relates generally to instruments for penile prosthesis implantation. More particularly, the invention relates to an insertion tool particularly useful for inserting the proximal end of an implantable cylinder intended for implantation in the corpus cavernosum.

BACKGROUND OF THE INVENTION

Implantable penile prostheses are available for treatment of erectile dysfunction, and various specialized tools exist for implanting such prostheses. A typical penile prosthesis includes at least one pair of cylinders that are each implantable in one of the corpus cavernosa and a pump external to the cylinder for pressurizing the cylinder. The pump is typically connected to the cylinder through a tubing near the proximal end of the cylinder.

Typical implantation tools, often provided to surgeons in kits, include tools for inserting the distal end of the cylinder, tools for measuring the proximal and distal ends of the cylinder, tools for sizing and tools for suturing the incision after implantation of the cylinder. Typically these tools have been made of stainless steel and are designed to be sterilized and reused repeatedly. Care must be taken to ensure that the surfaces of the tools remain smooth over time so as to avoid unnecessary injuries to the tissues at the implantation site.

There are no widely used tools specifically designed to assist in the implantation of the proximal cylinder end of penile prosthesis. There is thus a continuing need for penile implantation tools of this type that are safe, easy to use and versatile. The invention disclosed herein is aimed at providing a tool that achieves one or more of these goals while having substantially fewer drawbacks of the conventional tools.

SUMMARY OF THE INVENTION

Generally, the invention provides a device for inserting a penile implant prosthesis through an incision into a corpus cavernosum. The device includes an elongated, rigid body having a tip portion and tail portion, the tip portion including two prongs extending in a tip direction and a center portion between the two prongs, the prongs and center portion defining a notch adapted to engage and exert a force along the tip direction on a corner where a cylinder portion and a pump tubing of the prosthesis join each other, the prongs and center portion further defining a recess on one side of the center portion, the recess adapted to at least partially receive the cylinder portion or the pump tubing.

The elongated body of the device can define a channel disposed along a substantial portion of the elongated body. The tail portion of the elongated body can be formed as a paddle adapted to be inserted between the cylinder and tissues near or at the incision to prevent puncturing of the cylinder when the incision is being sutured closed. The tail portion can also be a rounded tail end adapted to engage an end of the cylinder portion for pushing the cylinder portion into the corporal body.

The tip portion can extend either in a direction parallel to the longitudinal axis of the elongated body or form an angle with it, depending on the desired operation.

BRIEF DESCRIPTION OF THE DRAWINGS

Other objects and advantages of the invention will become apparent upon reading the following detailed description and upon reference to the drawings in which:

FIG. 2 schematically shows the plan view of the insertion tool according to one aspect of the invention;

FIG. 3 schematically shows the longitudinal cross-section view of the insertion tool shown in FIG. 2;

FIG. 4 schematically shows the side view of the insertion tool shown in FIG. 2;

FIG. 5 schematically shows an axial cross-sectional view of the handle portion of the insertion tool shown in FIG. 2;

FIG. 6 schematically shows an axial cross-sectional view of the neck portion of the insertion tool shown in FIG. 2;

FIG. 7 schematically shows a more detailed view of the tip region of the insertion tool shown in FIG. 2;

FIG. 8 schematically shows a tip-end view of the insertion tool shown in FIG. 2;

FIG. 9 schematically shows the plan view of the an insertion tool according to another aspect of the invention;

FIG. 10 schematically shows the longitudinal cross-section view of the insertion tool shown in FIG. 9;

FIG. 11 schematically shows the side view of the insertion tool shown in FIG. 9;

Figure 1:
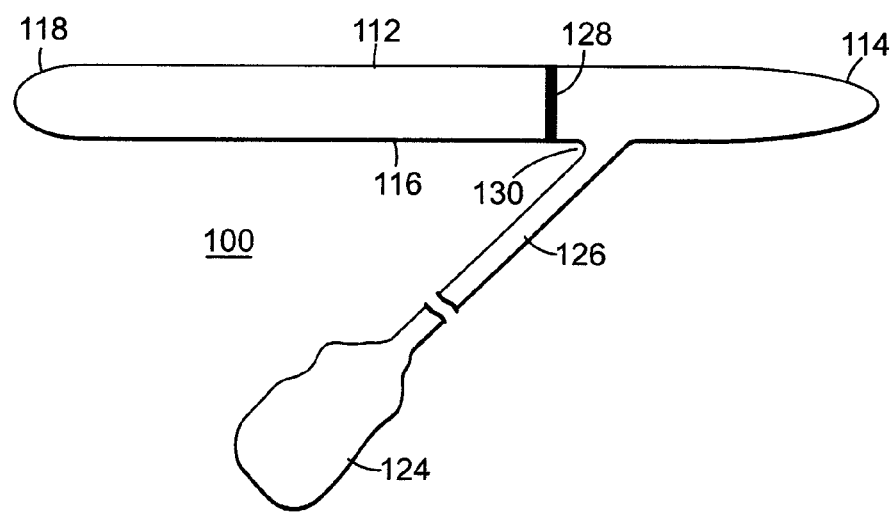
FIG. 1 schematically illustrates a penile implant prosthesis the implantation of which the insertion tool of the invention is particularly useful.
Figure 13:
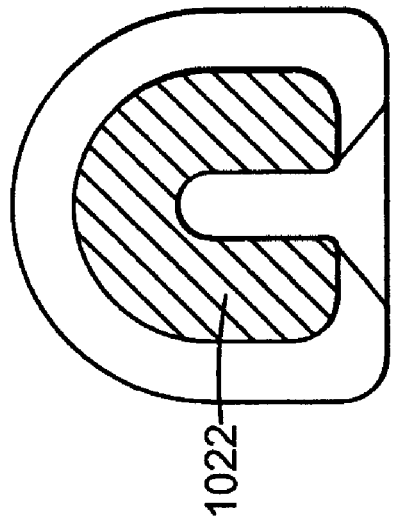
FIG. 13 schematically shows an axial cross-sectional view of the neck portion of the insertion tool shown in FIG. 9.
Figure 12:
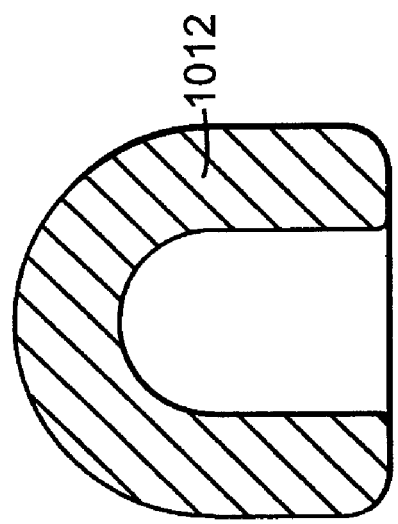
FIG. 12 schematically shows an axial cross-sectional view of the handle portion of the insertion tool shown in FIG. 9.
Figure 14:
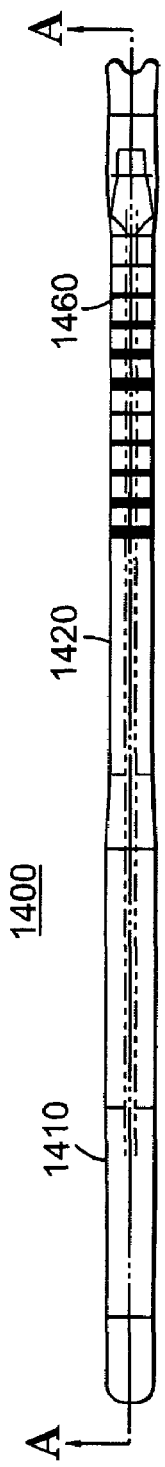
FIG. 14 schematically shows the plan view of the an insertion tool according to another aspect of the invention.
Figure 15:
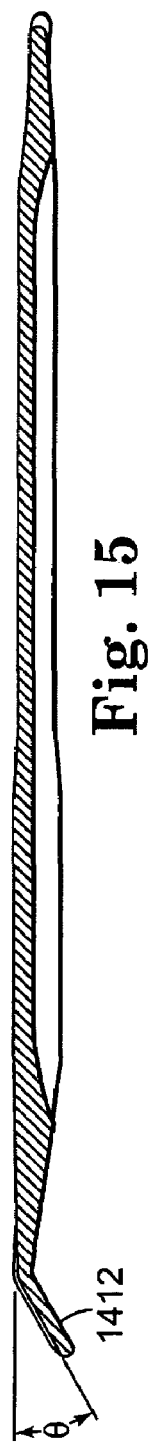
FIG. 15 schematically shows the longitudinal cross-section view of the insertion tool shown in FIG. 14.
Figure 16:
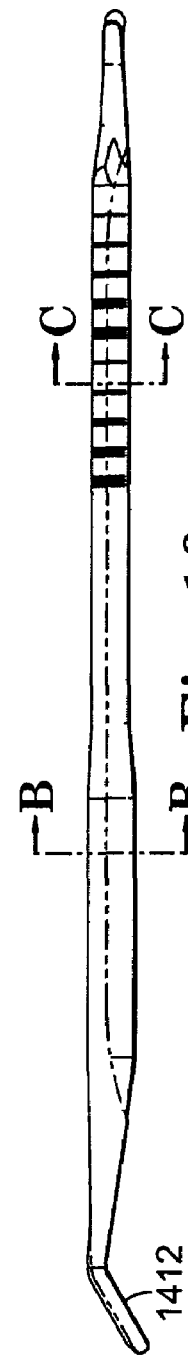
FIG. 16 schematically shows the side view of the insertion tool shown in FIG. 14.
Figure 19:
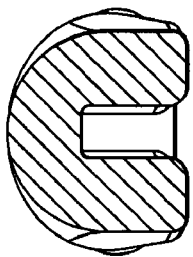
FIG. 19 schematically shows an axial cross-sectional view of the neck portion of the insertion tool shown in FIG. 14.
Figure 21:
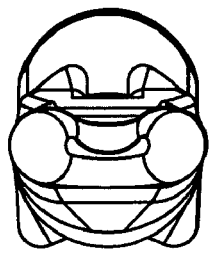
FIG. 21 schematically shows a tip-end view of the insertion tool shown in FIG. 14.
Figure 18:
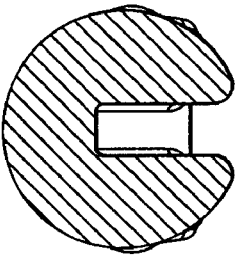
FIG. 18 schematically shows an axial cross-sectional view of the handle portion of the insertion tool shown in FIG. 14.
Figure 20:
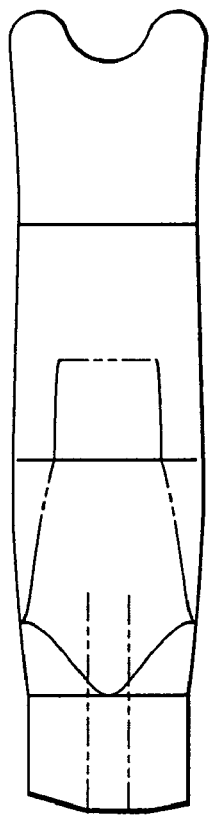
FIG. 20 schematically shows a more detailed view of the tip region of the insertion tool shown in FIG. 14.
Figure 17:
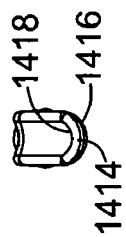
FIG. 17 schematically shows the tail-end view of the insertion tool shown in FIG. 14.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Referring to FIG. 1, a penile implant prosthetic device 100, for the insertion tool of the invention is particularly useful, includes a cylinder or tubular enclosure 112, implantable in a corpus cavernosum, a pump bulb 124, to be disposed outside corpus cavernosum (typically implanted in the scrotum), and a tubing 126 connecting the cylinder 112 and the bulb 124. The cylinder 112 includes a proximal portion 114, a medial portion 116 and a distal portion 118. The medial portion 116 is flexible and can be pressurized by fluid pumped from the bulb 124 via the tubing 126. The proximal portion 114 is substantially more rigid the medial portion 116 and includes the junction 128 between the cylinder 112 and tubing 126. The cylinder 112 and tubing 126 typically form a corner 130 that has an acute angle.

Referring to FIGS. 2 through 8, the insertion tool 200 in one embodiment of the invention has an elongated shape and includes a substantially round handle portion 210, a thinner, neck portion 220 having a U-shaped cross-section, a connecting portion 230 connecting the neck portion 220 to the handle portion 210, and a tip portion 240. The tool 200 in this embodiment is about 8.7" long and about 0.32" across in the handle portion 210, but can be of other sizes depending on the particular application.

The tip portion 240 includes a center portion 242 flanked by two round-edged prongs 244 and 246. Together, the center portion 242 and prongs 244, 246 define a round notch 248 with a diameter of about 0.15". Furthermore, the center portion 242 is thinner than the prongs 244, 246. The center portion 242 in this case also has an concave surface 842 (see FIG. 8). The center portion 242 and prongs 244, 246 therefore define a recess 850 having a concave bottom 842. The recess 850 with the concave bottom 842 can be pushed against either the cylinder 112 or the pump tubing 126 when the tool 200 is used to insert the cylinder 120 in to the corpus body. The tip portion 240 extends substantially in the same direction as the handle and neck portions 210 and 220, enabling the implantation operation to be carried out with the tool 200 disposed at substantially the same angle when the recess 850 faces either way.

The insertion tool 200 can be made of any suitable materials for surgical instruments. In the illustrative embodiment shown, the tool 200 is an integral device made of molded polyetherimide by known techniques, but can also be made of other materials such as other plastics, polymers and stainless steel. Tools made of plastics and/or polymeric materials typically can be economically made to be disposable. The material and dimensions of the tool 200 are chosen so that the tool 200 is substantially rigid, i.e., does not bend significantly under normal operating conditions for which the tool 200 is intended, or provides sufficient columnar strength to advance the proximal cylinder end within the corporal body.

The insertion tool 200 can also be partially or entirely coated with a layer of inert material that is compatible with both the penile prosthesis and human tissue, with both of which the tool 200 is likely to contact. For example, silicone or parylene can be applied to the tool 200 to produce a smoother surface, reducing the chances of injuring either the implant or tissue. The coated surface may also be more compatible with the surrounding tissue, reducing the probability of adverse reactions by the tissue. If the handle portion 210 is also coated, the coating can provide a more secure grip by the surgeon's gloved hand. The coating layer can be applied by a variety of known techniques, including simply dipping at least a portion of the insertion tool 200 in a suspension of the coating material and overmolding. The uncoated surfaces of the tool 200 can be deliberately roughened in preparation of coating to ensure superior bonding between the uncoated surfaces and the coating materials. Alternatively, one or more holes can be formed on the uncoated surfaces of the tool 200 so that dipped or overmolded material becomes mechanically attached to the tool 200 by one or more anchors formed in the hole(s).

The tail end 212 of the tool 200 in this embodiment is approximately semispherical with a radius of about 0.18".

The handle portion 210, neck portion 220 and the connecting portion 230 of the tool 200 further define a channel 310 running through most of the length of the tool 200 and ending near the tail end 212 and the tip portion 240. The channel 310 in this case has substantially the same width, about 0.07", throughout most of its length. The channel 310 has tapered ends 312 and 314 to reduce the chances of channel 310 catching any tissue during operation. The channeled structure enhances the rigidity of the tool 200 and facilitates reduction or elimination of bubbles during the molding processing of the plastic. The channel 310 can also serve to at least partially receive the cylinder 112 or pump tubing 126, depending on which way the tip recess 850 faces, during the implantation procedure.

In operation, the tool 200 can be used to push the proximal portion 114 of the cylinder into the corporal body with the notch placed at the corner 130 between the cylinder 112 and tubing 126. The tool 200 can be positioned with the recess 850 conforming to either the cylinder 112 or pump tubing 126, depending on where the operating physician desires to apply pressure. In some cases, it may also be desirable to use the round tail end 212 to push the proximal portion 114 at the end where the flexible medial portion 116 is attached.

Referring to FIGS. 9 through 13, a second embodiment of the invention is an insertion tool 900, which is similar to the tool 200 in the example above but has a tip 940 that curves "up" towards the tip end 942 (with the direction of the opening of the channel 1010 being "up"). Thus, while in the previous embodiment the tip portion 240 extends no higher than the top surface of the neck portion 220, the tip end 942 is above the top surface 924 of the neck portion 920 by about 0.09". The tip portion in this case extends in a direction at an angle θ (see FIG. 11) of about seven degrees from the longitudinal axis of the handle portion 910 and neck portion 920 but can be at other angles, such as between about five and ten degrees. This angled configuration results in a more secure engagement of the tool recess 950 with the cylinder 112 during the insertion operation as compared to a straight tip such as the tip 240 in the first embodiment.

The cross-sections of the handle portion 910, neck portion 920 and connection portion 930 are all substantially U-shaped in this illustrative embodiment. They collectively define a channel 1010 that has substantially the same thickness of the channel wall 1012 in the handle portion 910 as the channel wall 1022 in the neck portion 920. It is thought that having the same wall thickness throughout a molded plastic device may result in a more uniform plastic structure that is free of, or having significantly fewer, bubbles, voids and sink (or depression) spots, and offer improved columnar strength.

The tip portion 940 is also more streamlined than the tip portion 240 of the tool 200 in the previous example and can be more easily used as a suturing tool for protecting the cylinder from being punctured by the suturing needle when the incision is being closed after implantation of the cylinder. In such use, the concave surface of the tip is typically turn toward, and engaged to, the cylinder 112.

Referring to FIGS. 14 through 21, in a third illustrative embodiment of the invention, a insertion tool 1400 is similar to the tool 200 illustrated previously. However, instead having a round tail end 212, the tool 1400 has a tail segment 1412 that has a "downwardly"-curved wall 1414 having a concave "bottom" surface and convex "top" surface. Additionally, the tail segment 1412 in this embodiment extends in a direction at an angle Φ of about 28 degrees from the longitudinal axis of the handle and neck portions 1410, 1420, although other suitable angles, such as between about twenty and 35 degrees or between about fifteen and 45 degrees, can be used. The tail segment 1412 thus forms a paddle that makes the inserting tool 1400 also a closing tool, with the paddle 1412 used to protect the cylinder from being punctured by the suturing needle when the incision is being closed after implantation of the cylinder. Again, the concave surface is typically oriented to engage the cylinder surface 1418.

The insertion tool 1400 also includes several marks 1460 that are spaced apart from each other by predetermined distances. In this particular case the marks are about 0.394" (or 10 mm) apart. The marks serve as indicia of the depth of insertion. It should be noted that because the length of the proximal portion of the cylinder may be different in each patient's case, the marks 1460 are not indicative of the absolute depth but the distance from a predetermined reference point. The marks in this example are patterned such that each mark is visually distinct from its neighboring marks to facilitate easier tracking of the depth of insertion.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A device for inserting a penile implant prosthesis through an incision into a corpus cavernosum, the device comprising an elongated, rigid body having a tip portion and tail portion, the tip potion including two prongs extending in a tip direction and a center portion between the two prongs, the prongs and center portion defining a notch adapted to engage and exert a force along the tip direction on a corner where a cylinder portion and a pump tubing of the prosthesis join each other, the prongs and center portion further defining a recess on one side of the center portion, the recess adapted to at least partially receive the cylinder portion or the pump tubing, wherein the tail portion of the elongated body comprises a paddle having a concave surface adapted to be inserted between the cylinder and tissues near or at the incision to prevent puncturing of the cylinder when the incision is being sutured closed, and wherein the elongated body is disposed substantially along a longitudinal axis, and the paddle extends in a direction at least twenty degrees from the longitudinal axis.

2. The device of claim 1, wherein the tail portion of the body comprises a rounded tail end adapted to engage an end of the cylinder portion.

3. The device of claim 1, wherein the elongated body define a channel disposed along a substantial portion of the elongated body.

4. The device of claim 3, wherein the channel has two ends and a depth that diminishes gradually at both of the two ends.

5. The device of claim 3, wherein the elongated body is made of essentially a plastic material.

6. The device of claim 5, wherein the plastic material comprises polyetherimide.

7. The device of claim 1, further comprising an inert coating layer covering at least a portion of the elongated body.

8. The device of claim 7, where the inert coating layer covers substantially the entire elongated body.

9. The device of claim 7, wherein the inert coating layer comprises silicone.

10. The device of claim 1, wherein the elongated body is disposed substantially along a longitudinal axis, and the tip direction is substantially parallel to the longitudinal axis of the elongated body.

11. The device of claim 1, wherein the elongated body is disposed substantially along a longitudinal axis, and the tip direction forms an angle of at least five degrees with the longitudinal axis of the elongated body.

12. The device of claim 1, wherein the concave surface forms a bottom of the recess.

13. The device of claim 12, wherein the concave surface is adapted to be disposed to face the cylinder to prevent puncturing of the cylinder when the incision is being sutured closed.

* * * * *